US012213861B2

(12) United States Patent
Claessens

(10) Patent No.: US 12,213,861 B2
(45) Date of Patent: Feb. 4, 2025

(54) SMALL ANIMAL ANESTHETIZATION GAS MASK WITH INTEGRATED VALVE FUNCTION

(71) Applicant: Bruker Belgium N.V., Kontich (BE)

(72) Inventor: Timothy Claessens, Scherpenheuvel (BE)

(73) Assignee: Bruker Belgium N.V., Kontich (BE)

( * ) Notice: Subject to any disclaimer, the term of this patent is extended or adjusted under 35 U.S.C. 154(b) by 13 days.

(21) Appl. No.: 18/158,456

(22) Filed: Jan. 23, 2023

(65) Prior Publication Data

US 2023/0233306 A1    Jul. 27, 2023

(30) Foreign Application Priority Data

Jan. 25, 2022  (EP) .................................... 22153270

(51) Int. Cl.
*A61D 7/04*        (2006.01)

(52) U.S. Cl.
CPC ...................................... *A61D 7/04* (2013.01)

(58) Field of Classification Search
CPC .... A01K 1/031; A01K 13/001; A01K 1/0613; A61B 5/08; A61B 2503/40; A61B 5/0015; A61B 5/0022; A61B 5/0026; A61B 5/0033; A61B 5/055; A61B 5/0833; A61B 5/0836; A61B 5/087; A61B 5/0871; A61B 5/097; A61B 5/4821; A61B 5/6898; A61B 5/702; A61B 5/704; A61B 5/7207; A61B 5/7278; A61B 5/742; A61B 6/03; A61B 6/032; A61B 6/037; A61B 6/04; A61B 6/0421; A61B 6/0428; A61B 6/045;

(Continued)

(56) References Cited

U.S. PATENT DOCUMENTS

| 733,027 A | * | 7/1903 | Goldan | ................. | A61M 16/18 128/203.28 |
| 955,121 A | * | 4/1910 | Hollett | ................. | A61M 16/18 128/203.25 |

(Continued)

FOREIGN PATENT DOCUMENTS

| BE | 564566 A | 7/1960 |
| CH | 696 184 A5 | 2/2007 |

(Continued)

*Primary Examiner* — Annette Dixon
(74) *Attorney, Agent, or Firm* — Orbit IP, LLP; Marc G. Martino

(57) ABSTRACT

An anesthetization gas mask for a small animal includes a first mask part providing an inlet for an anesthetization gas and a second mask part for transmitting the anesthetization gas. The first and the second mask part define an anesthetization volume for receiving an animal's mouth part. The second mask part transmitting the anesthetization gas is movably connected to the first mask part having the inlet for an anesthetization gas. The anesthetization gas mask is geometrically constructed such that a movement of the first mask part from a working position to a blocking position relative to the second mask part blocks the passage of anesthetization gas into the anesthetization volume. This anesthetization gas mask has a valve function integrated in the mask system itself, so that anesthesia gas is not spilled when not in use and with a fixed geometry so that the extraction is always present when handled.

17 Claims, 5 Drawing Sheets

(58) Field of Classification Search
CPC ..... A61B 6/0487; A61B 6/4417; A61B 6/508; A61D 7/04; A61D 2003/003; A61D 3/00; A61J 17/001; A61J 7/0053; A61M 16/0009; A61M 16/0048; A61M 16/009; A61M 16/01; A61M 16/06; A61M 16/0816; A61M 16/0875; A61M 16/104; A61M 16/18; A61M 16/186; A61M 2205/3368; A61M 2205/3653; A61M 2205/84; A61M 2230/435; A61M 1/804; A61M 11/06; A61M 15/00; A61M 15/0016; A61M 15/0018; A61M 15/0021; A61M 15/0086; A61M 15/009; A61M 15/08; A61M 16/00; A61M 16/0006; A61M 16/0045; A61M 16/0051; A61M 16/0057; A61M 16/0075; A61M 16/0078; A61M 16/0084; A61M 16/024; A61M 16/0463; A61M 16/0468; A61M 16/0605; A61M 16/0611; A61M 16/0616; A61M 16/0633; A61M 16/0666; A61M 16/0683; A61M 16/08; A61M 16/0825; A61M 16/0833; A61M 16/085; A61M 16/0858; A61M 16/0866; A61M 16/10; A61M 16/101; A61M 16/1045; A61M 16/105; A61M 16/1055; A61M 16/106; A61M 16/1065; A61M 16/107; A61M 16/1085; A61M 16/12; A61M 16/122; A61M 16/125; A61M 16/127; A61M 16/14; A61M 16/16; A61M 16/167; A61M 16/20; A61M 16/201; A61M 16/202; A61M 16/204; A61M 16/205; A61M 16/206; A61M 16/207; A61M 16/208; A61M 16/209; A61M 2016/0015; A61M 2016/0021; A61M 2016/0027; A61M 2016/0039; A61M 2016/0661; A61M 2021/0016; A61M 2021/0044; A61M 21/02; A61M 2202/0007; A61M 2202/0085; A61M 2202/0208; A61M 2202/0225; A61M 2202/025; A61M 2202/0283; A61M 2202/0291; A61M 2202/048; A61M 2205/0216; A61M 2205/3334; A61M 2205/3375; A61M 2205/3379; A61M 2205/3553; A61M 2205/3584; A61M 2205/3592; A61M 2205/3606; A61M 2205/366; A61M 2205/42; A61M 2205/43; A61M 2205/505; A61M 2205/52; A61M 2205/583; A61M 2205/59; A61M 2205/75; A61M 2205/8225; A61M 2206/10; A61M 2206/14; A61M 2206/16; A61M 2207/00; A61M 2210/0618; A61M 2210/0625; A61M 2230/432; A61M 2240/00; A61M 2250/00; A61M 5/44; Y10S 128/91; Y10S 137/908; Y10S 128/03; Y10T 137/2544; Y10T 137/2569; Y10T 137/5283; Y10T 137/7757; Y10T 137/7764; Y10T 137/7766; Y10T 137/7781; Y10T 137/7843; Y10T 137/8309; Y10T 137/87595; Y10T 137/87627; Y10T 137/87917; A22B 3/00; A22B 3/005; A61G 13/1295; A61H 23/00; A62B 18/00; A62B 18/003; A62B 23/02; A62B 7/00; A62B 9/003; A62B 9/006; A62B 9/02; A62B 9/022; A63B 2208/12; A63B 2213/005; A63B 23/18; B63C 11/2227; F15C 1/008; F15C 1/04; F16K 11/076; F16K 31/1262; G01L 19/0023; G01L 7/084; G01R 33/5601; G01R 33/56366; G05D 11/006

See application file for complete search history.

(56) References Cited

U.S. PATENT DOCUMENTS

| | | | | |
|---|---|---|---|---|
| 2,990,838 | A * | 7/1961 | Cross | A61M 16/0048 137/908 |
| 3,505,998 | A * | 4/1970 | Brown | A61D 7/04 128/207.11 |
| 4,520,808 | A * | 6/1985 | LaBauve | A61B 5/08 128/203.29 |
| 4,770,169 | A | 9/1988 | Schmoegner et al. | |
| 4,896,666 | A * | 1/1990 | Hinkle | A61M 16/06 128/203.29 |
| 6,349,725 | B1 | 2/2002 | Perkins et al. | |
| 9,446,212 | B2 * | 9/2016 | Dunlop | A61M 16/01 |
| 2009/0084378 | A1 * | 4/2009 | Ichikawa | A61D 7/04 128/203.12 |
| 2012/0073509 | A1 * | 3/2012 | Rapoport | A61B 5/055 119/420 |
| 2021/0113317 | A1 | 4/2021 | Connelly | |

FOREIGN PATENT DOCUMENTS

| | | |
|---|---|---|
| CN | 111228625 A | 6/2020 |
| CN | 211561490 U | 9/2020 |
| CN | 213 077 081 U | 4/2021 |
| CN | 112891014 A | 6/2021 |

* cited by examiner

SMALL ANIMAL ANESTHETIZATION GAS MASK WITH INTEGRATED VALVE FUNCTION

CROSS-REFERENCE TO RELATED APPLICATIONS

This application claims priority to European Patent Application No. EP 22 153 270.8 filed Jan. 25, 2022, the entire contents of which are hereby incorporated in full by this reference.

DESCRIPTION

Field of the Invention

The invention relates to an anesthetization gas mask for a small animal comprising a first mask part providing an inlet for an anesthetization gas, a second mask part for transmitting the anesthetization gas being mechanically connected to the first mask part, wherein the first and the second mask part at least partially define an anesthetization volume for receiving a mouth part of the small animal.

BACKGROUND OF THE INVENTION

A mask for analyzed small animals comprising a cone, an inlet for gas and an extraction on the outside off the cone as well as a seal to prevent leakage is described in US 2012/0073509 A1 (=Reference [1]).

SUMMARY OF THE INVENTION

Technical Background of the Invention

In general, the present invention relates to the technical field of laboratory support for conducting scientific investigations on living animals. In particular, the invention contributes as an auxiliary aid for anesthetization of small animals, e.g., mice and rats, during examinations.

Reference [1] cited above describes a generic anesthetization gas mask for a small animal. For facilitating a gas flow, a flushing air device is provided. The gas flows from behind the anesthetization gas inlet and passes around the animal's head via a mask and plurality of apertures into a Bernoulli-type orifice being narrow relative to the widest diameter of the mask, via a hollow chamber of a housing, to an outlet and to a gas scavenger located outside the device for conduction the investigation on the animal. The inner part of the mask is of conical shape and has a plurality of apertures located in the outer circumference of the mask is to ensure effective flushing of air due to the irregular geometry of the animal's head, and to avoid blocking of air suction by the animal's body parts and fur.

No valve function for directly and manually influencing the gas flow is disclosed in Reference [1] for the mask system described therein, in particular no valve within near reach of the mask, but at best in spatial separation from the mask.

Generally, the already existing solutions according to prior art masks either use separated valves or exhibit an absence of any valve at all, so that test setups need to become adjusted.

OBJECTS OF THE INVENTION

It is an object of the present invention to provide—without much technical effort—a generic anesthetization gas mask for a small animal with a valve function integrated in the mask system itself, so that anesthesia gas is not spilled when not in use and with a fixed geometry so that the extraction is always present when handled. The new mask system should be easy to use, in particular for rats or mice, and easily to be applied in a wide variety of locations through it is small and compact construction.

BRIEF DESCRIPTION OF THE INVENTION

This object is achieved, in accordance with the present invention and in a surprisingly simple and effective way, by modifying an anesthetization gas mask as defined above in the first paragraph in that the second mask part for transmitting the anesthetization gas is movably connected to the first mask part having the inlet for an anesthetization gas, and in that the anesthetization gas mask is geometrically constructed and configured such that a rotatory or translatory movement of the first mask part from a working position to a blocking position relative to the second mask part blocks the passage of anesthetization gas into the anesthetization volume.

The anesthesia gas mask according to the invention is adapted for a single mouse or rat, the benefits being: it fits in a round bed from about 28 mm diameter; it can be locked when not used; the valve function can easily be operated manually just by moving the first mask part relative to the second mask part into an "open" or "closed" position; and it can be used with or without seal; the extraction is always present.

To supply anesthesia to a mouse, a gas mask according to the invention is placed over the nose from the animal, the used gas volume is low and the extraction is always in place.

Although the anesthetization gas mask according to the present invention is preferably used in devices for preclinical imaging, there are also other possible and useful implementations of the invention in further fields of research.

PREFERRED EMBODIMENTS AND FURTHER DEVELOPMENTS OF THE INVENTION

In straightforward embodiments of the invention, the anesthetization gas mask is geometrically constructed and configured such that the movement of the first mask part from the working position to the blocking position relative to the second mask part is a rotation. Although it is in principle possible to realize the present invention also with first and second mask parts being translatory moveable relative to each other, the technically easiest solution is a rotational movement. The benefits are: the rotation is implemented mostly related to the fact for the valve to open and close. It can look different when using translation, e.g., with a rectangular cross section (see below); this saves space since it does not increase the mask in any dimension; and further, it prevents that the small animal needs to be relocated on a bed for different valve positions, i.e., the small animal is put in place and a valve for transmission of anesthetization gas is opened then and vice versa before removing the animal.

In particularly preferred variants of these embodiments of the invention, the first mask part has a conical or cylindrical end and the second mask part has a conical or cylindrical receptacle for receiving the conical or cylindrical end of the first mask part. The benefits being that the different parts can easily be assembled and rotated when connected to each other, and the two mask parts have a greater spatial overlap, so that the anesthetic gas can be distributed more evenly in the anesthetic volume.

However, in special cases of application, there might be some need to avoid rotational movement. For these cases, alternative embodiments of the invention are suitable, where the anesthetization gas mask is geometrically constructed and configured such that the movement of the first mask part from the working position to the blocking position relative to the second mask part is a translation. The benefits being that the actual state of the valve could be easier determined since the mask/valve changes in size, and the flow of the anesthetic gas can be initiated together with the insertion of the small animal into the gas mask by, e.g., pushing both into one direction.

Possible is also a combination of rotation and translation, i.e., helical or spiral screw-thread type of movement.

Particularly preferred are variants of these embodiments, where the first mask part has a cuboid or prism-shaped end and the second mask part has a cuboid or prism-shaped receptacle for receiving the cuboid or prism-shaped end of the first mask part. The benefits being this would be required to block a rotation and the two mask parts have a greater spatial overlap, so that the anesthetic gas can be distributed more evenly in the anesthetic volume.

In another advantageous embodiment of the present invention, the inlet of the first mask part for the anesthetization gas is divided into several inlet channels and the second mask part has several first transmission channels for transferring the anesthetization gas, the respective channels each forming a common passage in the working position and being blocked against each other in the blocking position. By this means the anesthetic gas can be distributed more evenly in the anesthetic volume.

In a preferred further development of this embodiment, the inlet channels and the first transmission channels are arranged in a semicircular shape within the respective mask part. The benefits being: this refers to the rotational open/close mechanism; it provides the shortest path to combine the two parts; open and close position for gas inlet require only small rotation or translation of the mask parts with respect to each other; and semicircular arrangement is adapted to position of mouth of small animal, i.e., more efficient inhalation of the anesthetic gas below the mouth.

Another preferred embodiment of the invention is characterized in that the first mask part has an outlet for waste gas and the second mask part has second transmission channels for transmission of waste gas to the outlet of the first mask part. A benefit is having the waste gas removal at all and all included into a single mask. Further, the gas inlet and outlet are on the same side of the mask allowing for easier handling from the outside of a measurement instrument.

In an advantageous further development of this embodiment, the outlet of the first mask part splits into several outlet channels each forming a common passage together with the respective second transmission channels of the second mask part in the working position as well as in the blocking position. Depending on how the waste gas flows into the mask cone, the flow of gas might be more towards one side or the other. With several outlet channels it is more likely to remove most of the waste gas effectively. The outlet of gas is open in working as well as in blocking position therefor allowing passage of remaining anesthetic gas even if inlet is closed.

An alternative further development is characterized in that the outlet of the first mask part splits into several outlet channels each forming a common passage together with the respective second transmission channels of the second mask part in the working position and being blocked against each other in the blocking position. The open and close positions for the gas outlet require only a small rotation or translation of the mask parts with respect to each other.

Preferred is a variant of anyone of the above further development, in which the outlet channels of the first mask part and the second transmission channels of the second mask part form a circular shape in the respective mask part. The remaining anesthetic gas and the gas exhaled by the small animal ("exhaust" or "waste" gas) can be extracted more efficiently and uniformly from the anesthetic volume.

Also favorable is a class of embodiments of the invention, which are characterized in that the anesthetization gas mask comprises a cap-shaped third mask part having an opening for receiving a mouthpart of the small animal and being fixable to the second mask part. This third mask part is an optional feature. This can prevent that anesthesia gas is leaking from the cone into an imaging device and ultimately into the laboratory, where it could potentially harm personnel. Further, this limits the amount of anesthesia gas that is needed for sedating the small animal.

In this class of embodiments, the cap-shaped third mask part can be made of an elastic material, in particular of rubber. So, the rubber cap-shaped third mask part with a hole to place the nose of the animal in, provides an excellent seal function. However, the mask can work with or without this cap-shaped third mask part. In particular rubber will tightly fit the small animals nose minimizing gaps for leaks.

In another advantageous further development this class of embodiments, the cap-shaped third mask part has a slanted shape in the area of the opening. An advantage is a better fit of the mask onto the nose of a mouse or rat. The nose of those animals will never point 100% horizontal towards the end of the bed since the neck of the animal would have to be bent over.

Comparatively compact and simple embodiments of the anesthetization gas mask according to the present invention are characterized in that the second mask part has an opening for directly receiving a mouth part of the small animal and a slanted shape in the area of that opening. Again, this yields a better fit of the second mask onto the mouse or rat nose. The nose of those animals will never point 100% horizontal towards the end of the bed since the neck of the animal would have to be bent over. Furthermore transmission channels for transmission of waste gas to the outlet of the mask more effectively cover the shape of the nose or mouth of the small animal.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

BRIEF DESCRIPTION OF THE DRAWINGS

The invention is shown in the drawings. In such drawings.

DETAILED DESCRIPTION OF THE PREFERRED EMBODIMENTS

The present invention is principally concerned with providing tools for the anesthetization small animals, in particular with the development of an improved gas mask for a small animal.

Figure 1A:
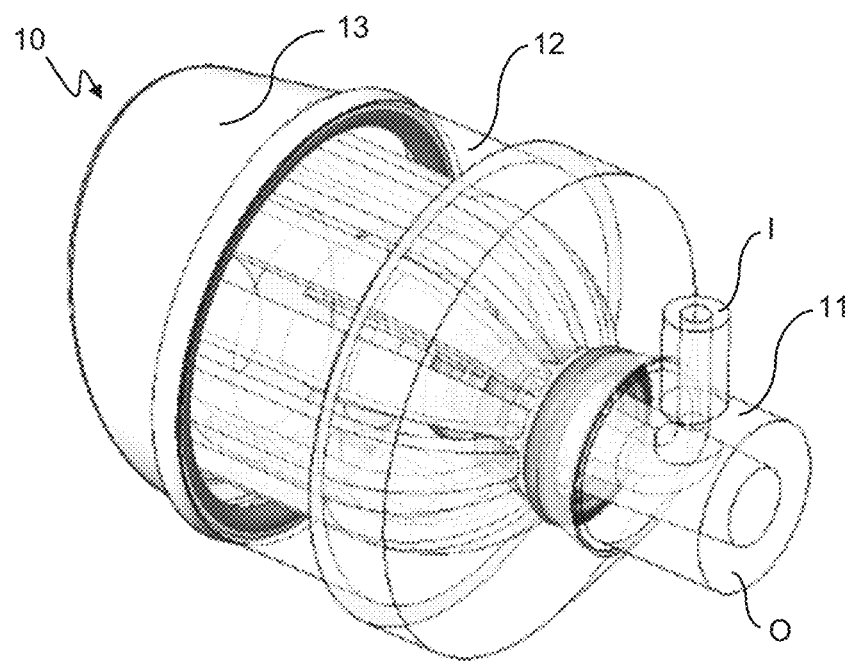
FIG. 1a shows a stereoscopic and partially transparent view of an embodiment of the anesthetization gas mask according to the invention.

FIG. 1a schematically and in a semi-transparent form depicts an anesthetization gas mask 10 for a small animal comprising a first mask part 11 providing an inlet I and an outlet O for an anesthetization gas, a second mask part 12 for transmitting the gas being mechanically connected to the first mask part 11, wherein the first and the second mask part 11, 12 at least partially define an anesthetization volume for receiving a mouth part of the small animal.

According to the present invention, this anesthetization gas mask 10 is characterized in that the second mask part 12 for transmitting the anesthetization gas is movably connected to the first mask part 11 having the inlet I for anesthetization gas, and that the anesthetization gas mask 10 is geometrically constructed and configured such that a movement of the first mask part 11 from a working position to a blocking position relative to the second mask part 12 blocks the passage of anesthetization gas into the anesthetization volume.

Figure 1B:
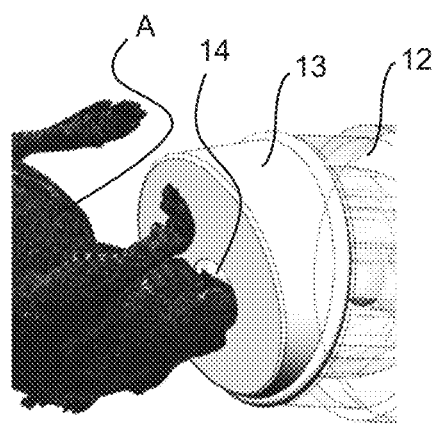
FIG. 1b shows a schematic partial view of a mouse with its mouth part inserted in an opening of a cap-shaped third mask part connected to an embodiment of the anesthetization gas mask according to the invention.

FIG. 1b shows a schematic partial view of a small animal A, in this case particularly a mouse, with its mouthpart inserted in an opening of a cap-shaped third mask part 13 connected to the anesthetization gas mask 10.

Figure 1C:
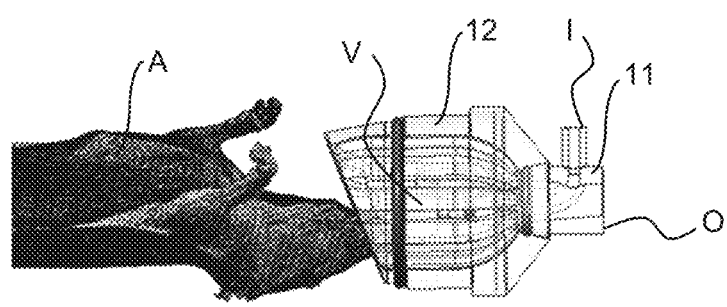
FIG. 1c shows in a side view the transparent embodiment of FIG. 1a with a cap-shaped third mask part applied to a mouse as in FIG. 1b.

FIG. 1c shows in a side view the transparent embodiment of FIG. 1a.

This embodiment of the anesthetization gas mask 10 is a three-parted mask with the first, second and third mask parts.

There are two separated channels inside the mask 10, one for the supply and one for the extraction from anesthesia mixture gas.

Figure 2:
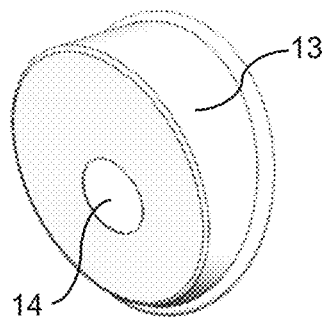
FIG. 2 shows in a stereoscopic view the cap-shaped third mask part of FIGS. 1a and 1b.

The stereoscopic view of FIG. 2 depicts the cap-shaped third mask part 13. The slanted shaped front face is there to make sure that over the tip of the nose from the mice is a good flow from the gas and oxygenic mixture.

The cap-like third mask part 13 is made of an elastic material, in particular of rubber, having a sealing function or being accompanied by extra sealing elements. There is an opening 14 to place the nose of the small animal A in and being fixable to the second mask part 12.

The anesthetization gas mask 10 can work with or without this cap-shaped third make part 13. Also without any additional seal, the mask 10 can be used and the gas extraction is still active and accurate.

Figure 3A:
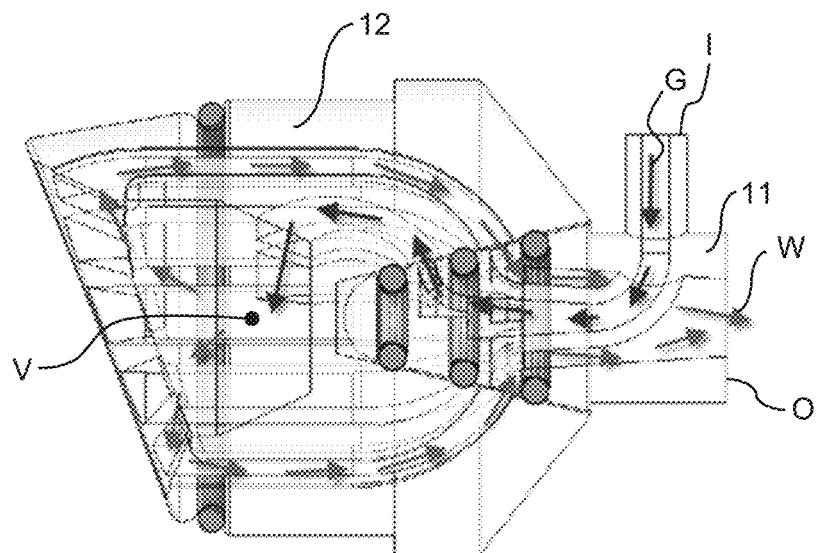
FIGS. 3a and 3b show—each in a semi-transparent side view—schematic vertical cross sections through embodiments of anesthetization gas mask according to the invention with the first and the second mask parts (a) in an "open" position with anesthetization gas flowing through the second mask part, and (b) in a "closed" position.
Figure 3B:
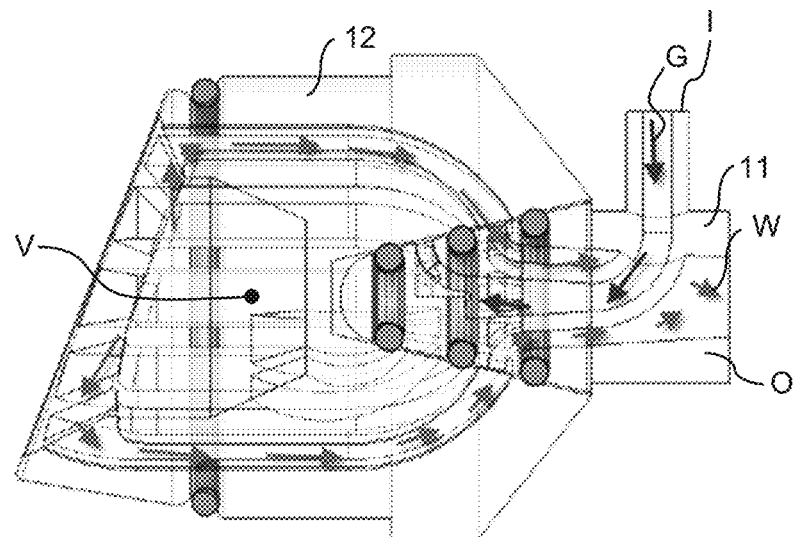

FIGS. 3a and 3b show—each in a semi-transparent side view with arrows depicting the flow of anesthetization gas G from the inlet I of the first mask part 11 to the anesthetization volume V and for transmission of exhaust or waste gas W to the outlet O of the first mask part 11—schematic vertical cross sections through embodiments of anesthetization gas mask according to the invention with the first and the second mask parts (a) in an "open" position with anesthetization gas G flowing from the first mask part 11 through the second mask part 12, and (b) rotated into a "closed" position for blocking the gas supply to the second mask part 12.

In this setup, the gas extraction is established for the whole anesthetization volume V in a circular arrangement while the gas insertion is made in an upper part, which is preferred if a small animal A is lying on its back. When the second mask part 12 is rotated by 180°, the supply of anesthetization gas G is blocked, but the extraction is still active. Generally, easy blocking is favorable when the mask is not in use.

The second part 12 of the mask 10 has a slanted structure to better fit the pointed shape of a small animal mouth.

In the embodiment shown in FIGS. 3a and 3b, the first mask part 11 has a conical end and the second mask part 12 has a conical receptacle for receiving the conical end of the first mask part 11. In other embodiments—not shown in the drawings—the first mask part may as well have a cylindrical end and the second mask part a cylindrical receptacle. Both embodiments allow a rotation of the first mask part with respect to the second mask part.

The schematic stereoscopic views of FIGS. 4a to 4d show an embodiment of the invention, where the anesthetization gas mask 10 is geometrically constructed and configured such that the movement of the first mask part 11 from the working position to the blocking position relative to the second mask part 12 is a rotation.

Figure 4A:
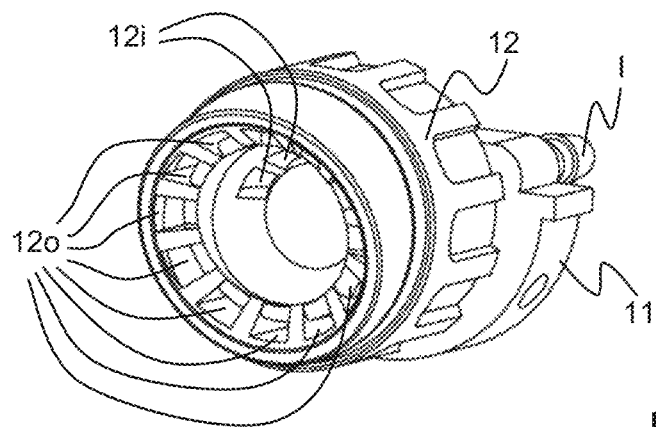
FIG. 4a shows a schematic stereoscopic view of an embodiment of the anesthetization gas mask according to the invention.
Figure 4B:
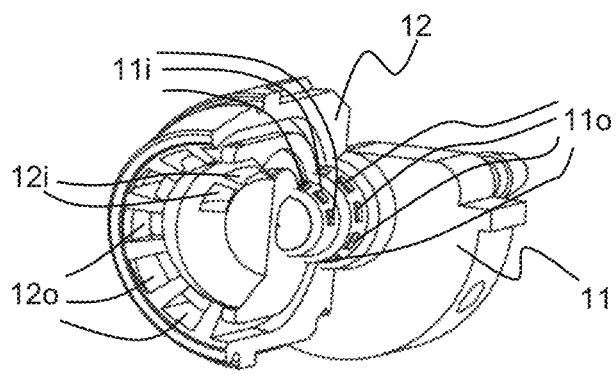
FIG. 4b shows the embodiment of FIG. 4a partially dismantled.
Figure 4C:
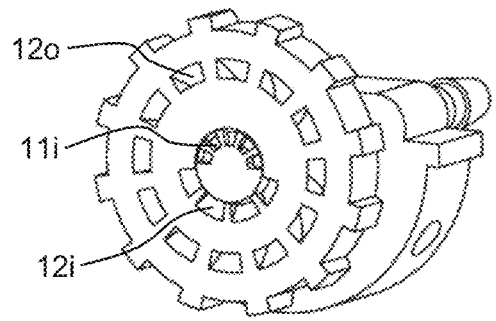
FIGS. 4c and 4d show a completely exposed interior part of the embodiment of FIG. 4a in (c) "closed" position and (d) "open" position of the first and second mask parts relative to each other.
Figure 4D:
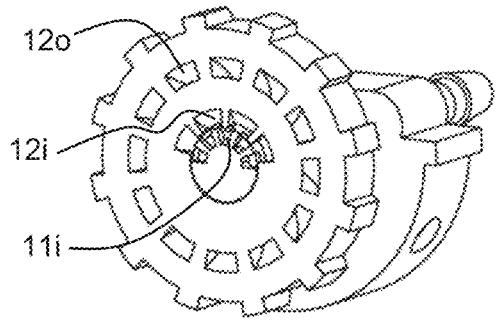

Whereas FIG. 4a shows the mask completely, FIG. 4b is depicting the mask partially dismantled and FIGS. 4c and 4d show a completely exposed interior part of the mask, namely FIG. 4c in a "closed" position and FIG. 4d in an "open" position of the first and second mask parts relative to each other.

The inlet I of the first mask part 11 for the anesthetization gas G is divided into several inlet channels 11i and the second mask part 12 has several first transmission channels 12i for transferring the anesthetization gas G, the respective channels 11i; 12i each forming a common passage in the working position and being blocked against each other in the blocking position. The inlet channels 11i and the first transmission channels 12i are arranged in a semicircular shape within the respective mask part 11; 12. Second transmission channels 12*o* are provided for transmission of waste gas W to the outlet O of the first mask part 11. The outlet channels 11*o* of the first mask part 11 and the second transmission channels 12*o* of the second mask part 12 form a circular shape in the respective mask part.

The outlet O of the first mask part 11 splits into several outlet channels 11*o* each forming a common passage together with the respective second transmission channels 12*o* of the second mask part 12 in the working position and being blocked against each other in the blocking position, in some embodiments also in the blocking position itself.

Figure 5A:
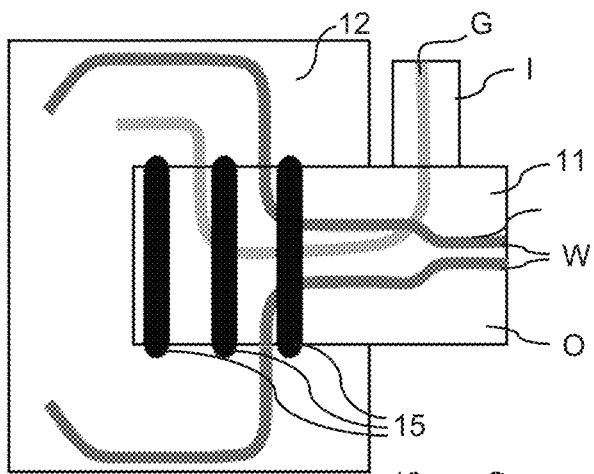
FIGS. 5a and 5b show schematic vertical cross sections through an embodiment of the anesthetization gas mask according to the invention with translational relative movement of the first and second mask parts in (a) "open" position and (b) "closed" position.
Figure 5B:
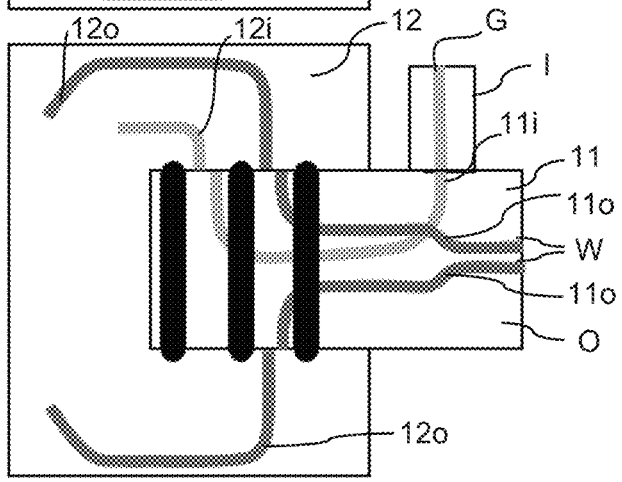

FIGS. 5*a* and 5*b* schematically depict the flow paths of anesthetization gas G and waste gas W through an embodiment of the anesthetization gas mask 10 with translational relative movement of the first mask part 11 and the second mask part 12 in (a) "open" position and (b) "closed" position for anesthetization gas G and waste gas W.

For effectuating a proper sealing also during relative movement between the first mask part 11 and the second mask part 12, sealing rings 15 are provided around the first mask part 11.

Figure 6:
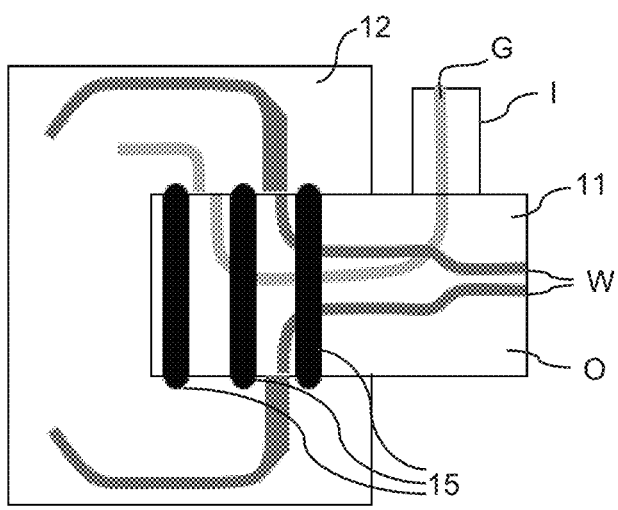
FIG. 6 shows a schematic vertical cross section through an alternative embodiment of the anesthetization gas mask according to the invention with translatory relative movement of the first and second mask parts in "closed" position.

In embodiments as shown in FIGS. 5*a*, 5*b* and 6, the first mask part 11 has a cuboid or prism-shaped end and the second mask part 12 has a cuboid or prism-shaped receptacle for receiving the cuboid or prism-shaped end of the first mask part 11.

FIG. 6 shows a schematic vertical cross section through an alternative embodiment of the invention, where the anesthetization gas mask 10 is geometrically constructed and configured such that the movement of the first mask part 11 from the working position to the blocking position ("closed") relative to the second mask part 12 blocks only the anesthetization gas G. Waste gas W is still transmitted to the outlet.

Figure 7:
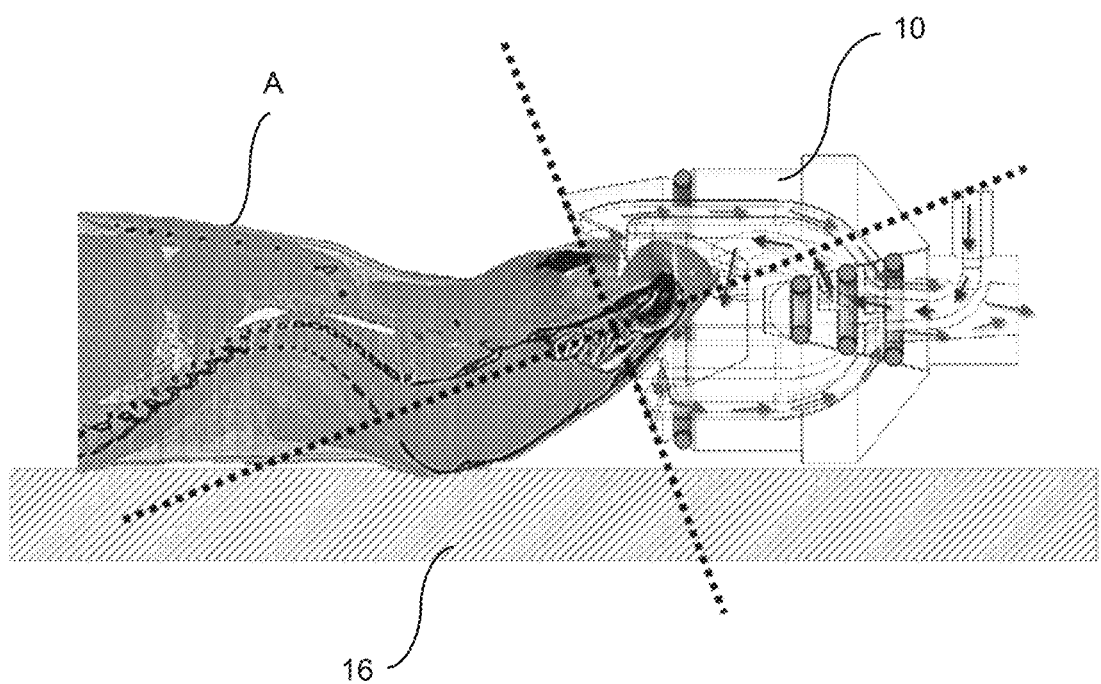
FIG. 7 shows a small animal lying on a bed with its nose pointing into the anesthetization mask in a schematic vertical cross section.

FIG. 7 shows the anesthetization mask 10 coupled to a small animal bed 16. Such beds are, e.g., used in MR, CT, PET imaging systems. The small animal A as typical for such imaging applications is laying on its back with its nose pointing into the anesthetization mask 10, thereby forming a right angle with the slanted surface of the mask. The slanted front of the second mask part (indicated by a first dotted line) avoids the neck of the animal to be bent over when inserted into the mask. This is true for the small animal lying either on back or on belly. Thus, having a slanted surface, the mask will better fit onto the animal's nose.

LIST OF REFERENCE SIGNS

10 anesthetization gas mask
11 first mask part
11*i* inlet channels
11*o* outlet channels
12 second mask part
12*i* first transmission channels
12*o* second transmission channels
13 cap-shaped third mask part
14 opening for receiving a mouth part
15 sealing ring
16 small animal bed
A small animal
G anesthetization gas
I inlet for anesthetization gas
O outlet for waste gas
V anesthetization volume
W waste gas

PRIOR ART CITATIONS

Publications considered for assessing patentability of the present invention:
[1] US 2012/0073509 A1

What is claimed is:

1. An anesthetization gas mask for a small animal, comprising:
   a first mask part providing an inlet for an anesthetization gas;
   a second mask part for transmitting the anesthetization gas being mechanically connected to the first mask part;
   wherein the first and the second mask part at least partially define an anesthetization volume for receiving a mouth part of the small animal;
   wherein the second mask part for transmitting the anesthetization gas is movably connected to the first mask part, the first mask part manually movable by a user back and forth relative to the second mask part between a working position and a blocking position;
   wherein the first mask part and the second mask part cooperatively form a valve, the valve configured to either block or transmit the anesthetization gas flowing in either direction between the inlet and the anesthetization volume depending on whether the first mask part and the second mask part are in the working position or the blocking position;
   and wherein the anesthetization gas mask is geometrically constructed and configured wherein a movement operated manually of the first mask part by the user from the working position to the blocking position relative to the second mask part blocks the passage of anesthetization gas through the valve into the anesthetization volume.

2. The anesthetization gas mask according to claim 1, wherein the anesthetization gas mask is geometrically constructed and configured wherein the movement of the first mask part by the user from the working position to the blocking position relative to the second mask part is a rotation.

3. The anesthetization gas mask according to claim 2, wherein the first mask part has a conical or cylindrical end and the second mask part has a conical or cylindrical receptacle configured for receiving the conical or cylindrical end of the first mask part.

4. The anesthetization gas mask according to claim 1, wherein the anesthetization gas mask is geometrically constructed and configured wherein the movement of the first mask part by the user from the working position to the blocking position relative to the second mask part is a translation.

5. The anesthetization gas mask according to claim 4, wherein the first mask part has a cuboid or prism-shaped end and the second mask part has a cuboid or prism-shaped receptacle for receiving the cuboid or prism-shaped end of the first mask part.

6. The anesthetization gas mask according to claim 1, wherein the inlet of the first mask part for the anesthetization gas is divided into several inlet channels and the second mask part has several first transmission channels configured for transferring the anesthetization gas, the respective channels each forming a common passage in the working position and being blocked against each other in the blocking position.

7. The anesthetization gas mask according to claim 6, wherein the inlet channels and the first transmission channels are arranged in a semicircular shape within the respective mask part.

8. The anesthetization gas mask according to claim 1, wherein the first mask part has an outlet for waste gas and the second mask part has second transmission channels for transmission of waste gas to the outlet of the first mask part.

9. The anesthetization gas mask according to claim 8, wherein the outlet of the first mask part splits into several outlet channels each forming a common passage together with the respective second transmission channels of the second mask part in the working position as well as in the blocking position.

10. The anesthetization gas mask according to claim 9, wherein the outlet channels of the first mask part and the second transmission channels of the second mask part form a circular shape in the respective mask part.

11. The anesthetization gas mask according to claim 8, wherein the outlet of the first mask part splits into several outlet channels each forming a common passage together with the respective second transmission channels of the second mask part in the working position and being blocked against each other in the blocking position.

12. The anesthetization gas mask according to claim 11, wherein the outlet channels of the first mask part and the second transmission channels of the second mask part form a circular shape in the respective mask part.

13. The anesthetization gas mask according to claim 1, wherein the anesthetization gas mask comprises a third mask part having an opening for receiving a mouth part of the small animal and being fixable to the second mask part.

14. The anesthetization gas mask according to claim 13, wherein the third mask part is made of an elastic material.

15. The anesthetization gas mask according to claim 14, wherein the elastic material of the third mask part is rubber.

16. The anesthetization gas mask according to claim 13, wherein the third mask part has a slanted shape in the area of the opening.

17. The anesthetization gas mask according to claim 1, wherein the second mask part has an opening configured for directly receiving a mouth part of the small animal and a slanted shape in the area of that opening.

\* \* \* \* \*